United States Patent [19]

Heller

[11] Patent Number: 4,567,882

[45] Date of Patent: Feb. 4, 1986

[54] METHOD FOR LOCATING THE ILLUMINATED TIP OF AN ENDOTRACHEAL TUBE

[75] Inventor: Richard M. Heller, Nashville, Tenn.

[73] Assignee: Vanderbilt University, Nashville, Tenn.

[21] Appl. No.: 680,242

[22] Filed: Dec. 10, 1984

Related U.S. Application Data

[63] Continuation of Ser. No. 446,965, Dec. 6, 1982, abandoned, which is a continuation-in-part of Ser. No. 212,210, Dec. 2, 1980, abandoned.

[51] Int. Cl.[4] .............................................. A61B 1/06
[52] U.S. Cl. .......................................... 128/11; 128/6; 128/665; 604/21
[58] Field of Search ........................................ 128/4–8, 128/11, 23, 200.26, 653, 654, 656, 658, 664; 362/32, 804; 604/20, 21

[56] References Cited

U.S. PATENT DOCUMENTS

| | | | |
|---|---|---|---|
| 922,985 | 5/1909 | Wappler | 128/4 |
| 1,667,630 | 4/1928 | Loeck | 128/6 |
| 1,704,764 | 3/1929 | Schellberg | 128/6 |
| 2,235,979 | 3/1941 | Brown | 128/6 |
| 2,797,683 | 7/1957 | Aiken | 128/6 |
| 3,068,737 | 12/1962 | Hicks et al. | 128/634 |
| 3,131,690 | 5/1964 | Innis et al. | 128/23 |
| 3,456,641 | 7/1969 | Yokata et al. | 128/4 |
| 3,527,982 | 9/1970 | Thomas | 128/653 |
| 3,672,352 | 6/1972 | Summers | 128/2 R |
| 3,693,623 | 9/1972 | Harte et al. | 128/303.1 |
| 3,866,599 | 2/1975 | Johnson | 128/6 |
| 4,096,862 | 6/1978 | DeLuca | 128/348 |
| 4,244,362 | 1/1981 | Andersen | 128/200.26 |
| 4,248,214 | 2/1981 | Hannah et al. | 128/7 |
| 4,286,602 | 9/1981 | Guy | 128/665 |
| 4,306,547 | 12/1981 | Lowell | 128/11 |
| 4,311,138 | 1/1982 | Sugarman | 604/21 |
| 4,312,357 | 1/1982 | Andersson et al. | 128/664 |

FOREIGN PATENT DOCUMENTS 2805451  8/1978  Fed. Rep. of Germany .......... 128/6

Primary Examiner—Edward M. Coven
Assistant Examiner—Max F. Hindenberg
Attorney, Agent, or Firm—Tilton, Fallon, Lungmus

[57] ABSTRACT

An improvement in catheters and other medical tubes and in the method of use thereof, which facilitates the precise positioning of the tips of such tubes within body passages. The improved method and device are particularly useful in the care and treatment of premature infants. The medical tube has a fiberoptic light conductor extending lengthwise through the wall thereof, the conductor ending in a light emitting and redirecting terminus adjacent the tube's free or distal end. The opposite end of the conductor is operatively connected to an external source of high-intensity light in the visible range. Light emitted laterally from the tip of such an indwelling tube may be visually and externally observed through the body wall of the patient for accurately and quickly determining the anatomical location of that tip. In a preferred embodiment, the tube is formed of transparent, flexible, thermoplastic material and the light-emitting terminus of the conductor is beveled and is completely embedded within the wall of the tube, so that light emitted from the terminus must pass through the tube's transparent wall.

5 Claims, 12 Drawing Figures

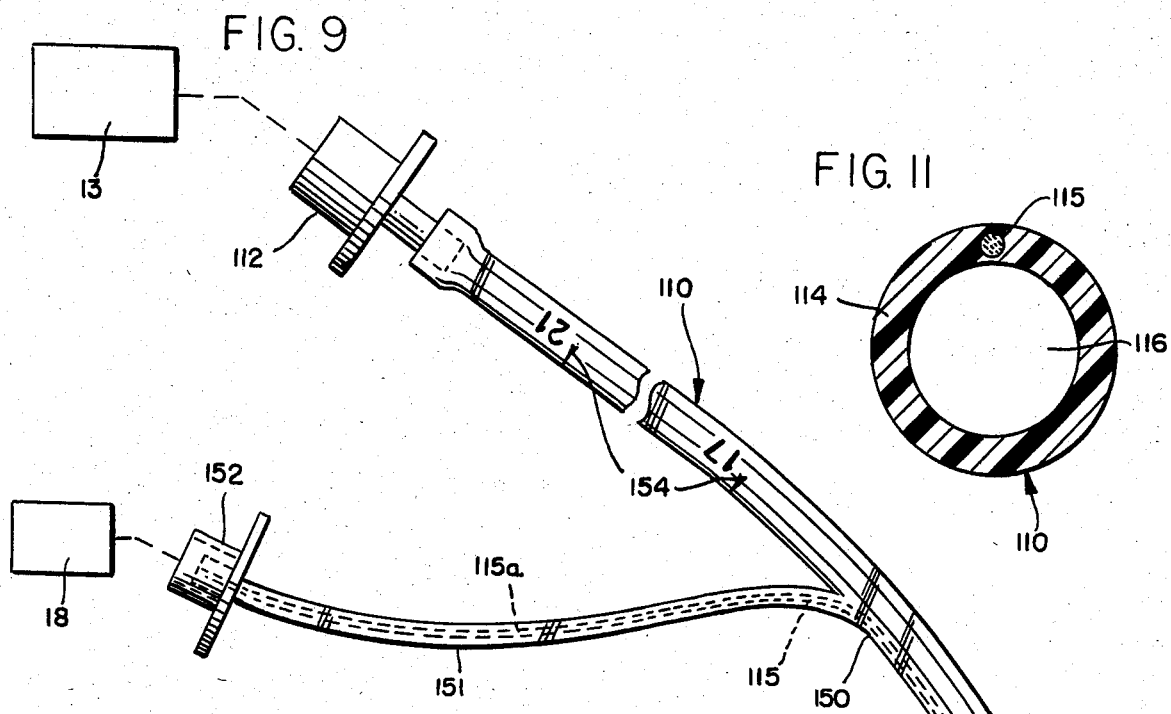
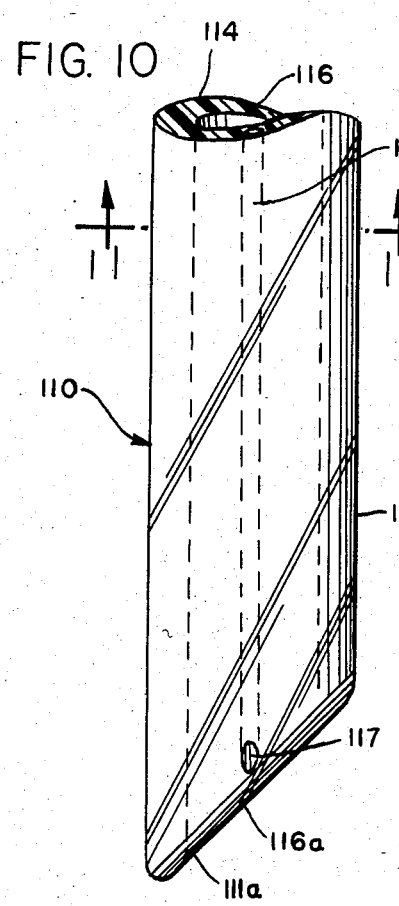
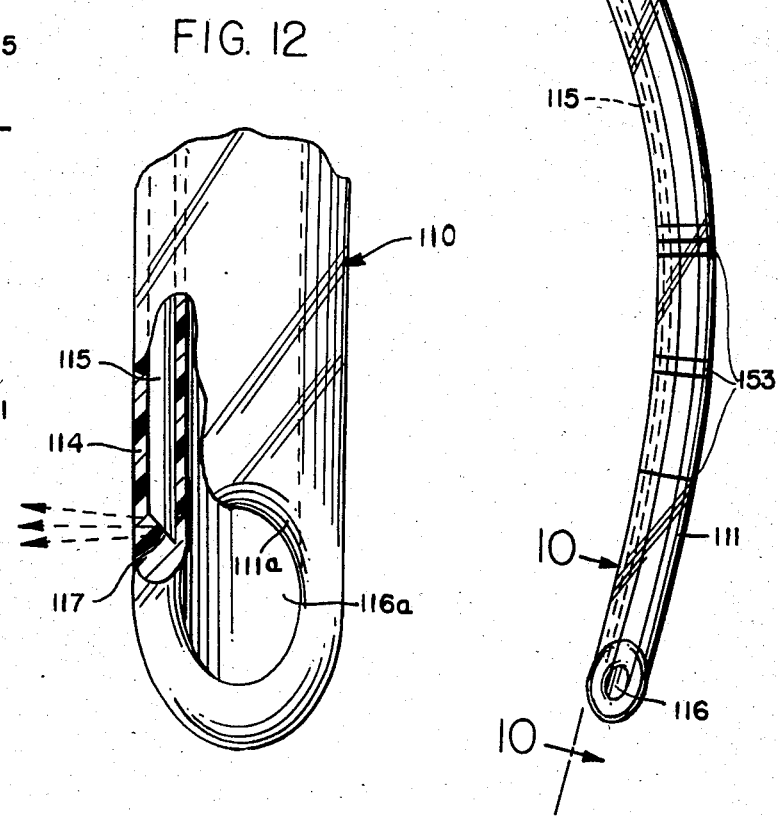
FIG. 9
FIG. 11
FIG. 10
FIG. 12

METHOD FOR LOCATING THE ILLUMINATED TIP OF AN ENDOTRACHEAL TUBE

RELATED APPLICATIONS

This application is a continuation of my copending application Ser. No. 446,965, filed Dec. 6, 1982, which in turn was a continuation-in-part of my application Ser. No. 212,210, filed Dec. 2, 1980 abandoned.

BACKGROUND AND SUMMARY

A major problem in the care of premature infants is the correct placement of endotracheal tubes, orogastric tubes, umbilical artery and venous catheters. Not only must these tubes be placed in the appropriate positions, but they must be maintained in such positions throughout the treatment periods.

For example, premature babies are frequently sustained on a mixture of oxygen and air which flows into the baby's lungs through an endotracheal tube. Obviously, if the endotracheal tube is in an incorrect position, possibly either too high or too low, either one lung will not be ventilated at all or, if the tube is above the vocal cords, neither lung will be ventilated. Radiographs are commonly taken, sometimes at frequent intervals, to establish that such an endotracheal tube has been and remains properly located.

Similarly, premature infants are often fed with orogastric tubes, such a tube extending through the mouth and into the infant's stomach. Again, radiographs are ordinarily taken to be certain that the tube ends in the patient's stomach and not in the duodenum or jejunum. The same principles apply to the placement of umbilical artery catheters and umbilical venous catheters; such catheters must be located precisely with regard to established reference points, notably the vertebral bodies, so that such catheters do not jeopardize the vessels leading from the aorta or the veins leading to the inferior venacava.

Frequent repeated exposure to ionizing radiation carries obvious risks and disadvantages whether the patient is a premature infant, an older child, or an adult. The problems described above are by no means limited to the treatment of premature infants although they tend to be accentuated because of the duration of the treatment and because handling and movement of such a patient necessitate periodic rechecking of tube placement. The time and effort involved in making frequent chest radiographs may be considerable, and add significantly to the cost of caring for and treating a premature infant.

It is therefore an object of this invention to provide an improved invasive medical tube, and its method of use, which allow a physician or nurse to locate and position the tip of such a tube in a body passage without resort to radiographic assistance. Another object is to provide a method for locating the tip of a catheter or other indwelling medical tube, and for quickly and easily positioning or repositioning that tip, without exposing the patient to potentially harmful ionizing radiation. A still further object is to provide a faster and easier, as well as safer, method and means for anatomically locating, and if necessary relocating, the tip of an indwelling catheter or other medical tube.

Briefly, the invention involves providing an otherwise conventional transparent medical tube (the term "tube" being used herein to embrace catheters as well as air tubes, feeding tubes, and the like) with a fiberoptic light conductor extending longitudinally through the wall thereof and terminating adjacent the tube's distal end in light-emitting means which projects light from the conductor in at least one lateral direction. At the opposite or proximal end portion of the tube, the conductor is detachably connected to an external source of non-coherent high-intensity light in the visible range, that is, in the range of approximately 4000 to 7700 angstroms. To locate, and if necessary reposition, the tip of an indwelling tube, a user simply energizes the visible light source and ascertains the location of the tip by means of the light beamed laterally from the tip and visible through the body wall of the patient.

An aspect of this invention lies in the discovery that if the tip of a catheter is so illuminated with high intensity light in the visible range, and if such light is projected laterally in at least one direction adjacent such tip, the location of the tip within the body passage of a patient, as in the case of a premature infant, may be externally visually ascertained. The time, effort, expense, and risks of radiography may therefore be avoided.

The following patents are believed to indicate the state of the art: 3,672,352, 4,096,862, 3,776,222, 4,286,602, 4,025,776, 4,086,919, 2,235,831, 3,866,599, 3,831,017, 3,858,577, and 2,059,053 (UK).

DRAWINGS

FIG. 9 is a side elevational view of an endotracheal tube comprising a preferred embodiment of this invention.

FIG. 10 is an enlarged fragmentary elevational view taken along line 10—10 of FIG. 9.

FIG. 11 is a cross sectional view along line 11—11 of FIG. 10.

FIG. 12 is an elevational view of the tip portion of the endotracheal tube, shown partly in section to reveal the fiberoptic conductor therein.

DETAILED DESCRIPTION

Figure 1:
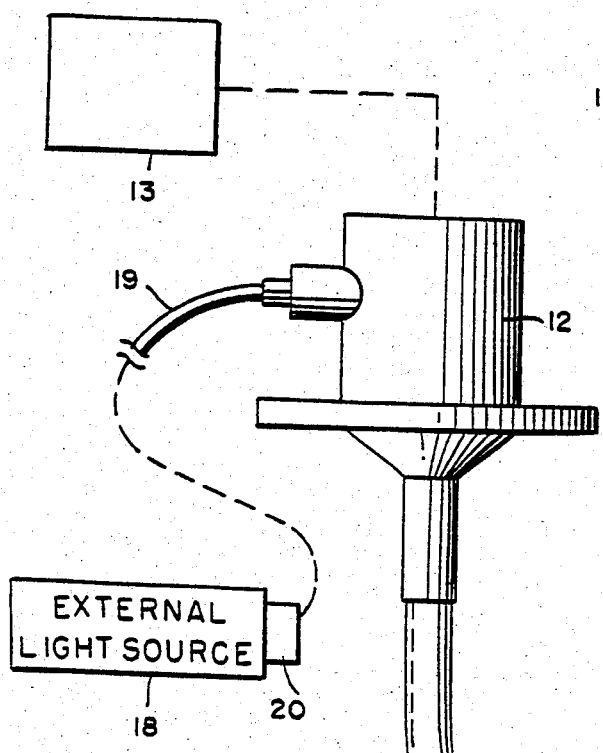
FIG. 1 is a side elevational view of an endotracheal tube equipped with the improvement of this invention.

Referring to the drawings, FIGS. 1–4 depict an endotracheal tube 10 having a distal tip portion 11 and a suitable connector 12 at its proximal end. The connector is adapted for connection by conventional means to a source 13 of an oxygen-air mixture.

For use as an endotracheal tube, tube 10 may have its wall formed of materials ranging from rigid to flexible and from opaque to transparent, although a material characterized as semi-rigid to flexible, and especially one which is translucent or transparent, is preferred. A plastic material such as polyvinyl chloride has been found particularly effective, but other plastics may be used and, in some cases, a more rigid material such as metal may be effective. In general, greater stiffness facilitates the insertion and positioning of an endotracheal tube; however, it is to be understood that an endotracheal tube is shown only for illustrative purposes and that where other uses are contemplated as, for example, where the tube is to function as an orogastric tube or as an umbilical artery or venous catheter, different materials having greater flexibility and resilience, as well as considerably different dimensions and proportions, would be selected. Since such differences are well known in the art, a more detailed discussion is believed unnecessary herein.

Figure 2:
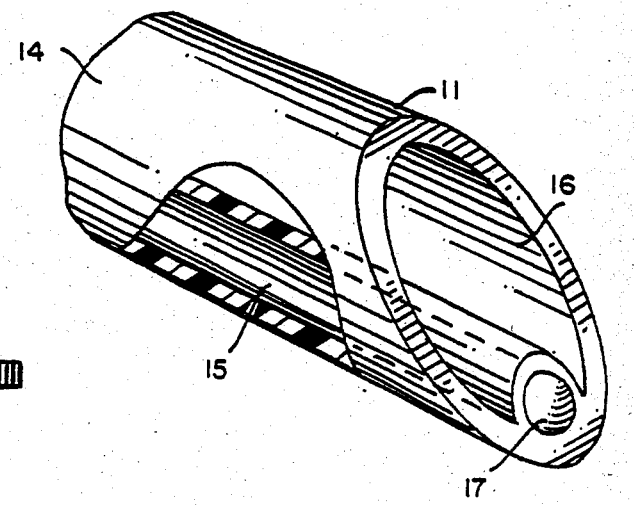
FIG. 2 is a three fourths perspective view of the tip of the tube.
Figure 3:
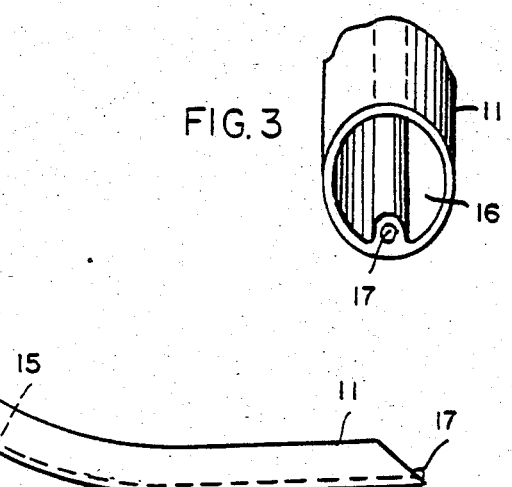
FIG. 3 is a top view in reduced scale of the tip construction depicted in FIG. 2.
Figure 4:
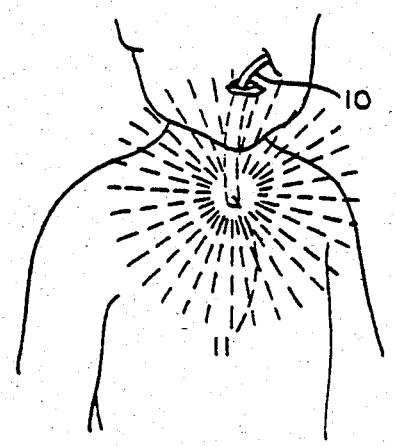
FIG. 4 illustrates the tube in use.

A fiberoptic light conductor 15, which may take the form of a single fiber or a bundle of such fibers of light-transmitting glass or plastic, extends longitudinally through the wall 14 of the tube as shown most clearly in FIGS. 1 and 2. The size of the conductor in relation to the tube may require the enlargement of the wall into a portion of lumen 16 (FIG. 2). At its distal end, the conductor is provided with light emitting means adjacent the distal end of the tube, such means permitting the unobstructed projection of light in at least one lateral direction. In the embodiment illustrated in FIGS. 1-4, the beveled end surface of the tube, and the position of emitter 17 axially beyond the major portion of that end surface, permits the radial or lateral projection of light about an arc well in excess of 300 degrees. Such a result may be achieved by forming the emitter as a glass bead which is either joined to or formed integrally with the conductor 15. Since the surface of the bead that projects axially beyond the end surface of the tube is rounded and generally semi-spherical in configuration, there is no reasonable possibility that the bead might abrade or otherwise injure delicate tissues as the tube is advanced along a body passage.

The conductor 15 emerges from connector 12 and extends to a source of high-intensity non-coherent light in the visible range between 4000 to 7700 angstroms. Light source 18 is diagramatically depicted in FIG. 1. Such light source may be entirely conventional and may take the form of the light boxes disclosed, for example, in U.S. Pat. Nos. 4,025,776 and 3,831,017. One effective light source utilizing a 150 watt incandescent light, is commercially available from Olympus Corporation of America, New Hyde Park, New York, under the designation ILK-3; however, other similar light boxes or light sources may be used. That portion of the conductor extending from connector 12 to light source 18 should be enclosed in a flexible protective casing or sheath, the attachment between cable 19 and the light source should be detachable (see the aforementioned patents), and a suitable switch 20 should be provided for manually turning the light source on and off.

In use, the endotracheal tube is extended through a patient's mouth and into the trachea to provide an airway for lung ventilation. The extent of insertion may be readily ascertained by energizing the light source 18 while conductor 15 is connected thereto. High-intensity light in the visible spectrum is transmitted through the wall of the endotracheal tube by the fiberoptic light conductor 15. Emitter 17, which in the embodiment of FIGS. 1-4 projects beyond a major portion of the distal end surface of the tube, redirects at least a substantial portion of the light laterally with the result that point illumination occurs at the endotracheal tube's distal end. Some of the light projected laterally and passing at generally right angles through the body wall of the patient may be externally received or observed by the naked eye, thereby permitting a qualified medical attendant to determine, and if necessary adjust, the anatomical position of the tip of the tube.

Figure 6:
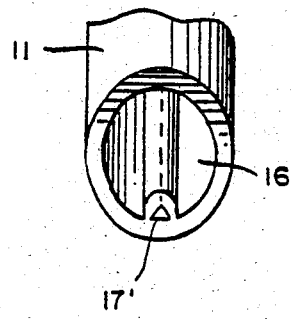
FIG. 6 is a top view in reduced scale of the tip construction of FIG. 5.
Figure 5:
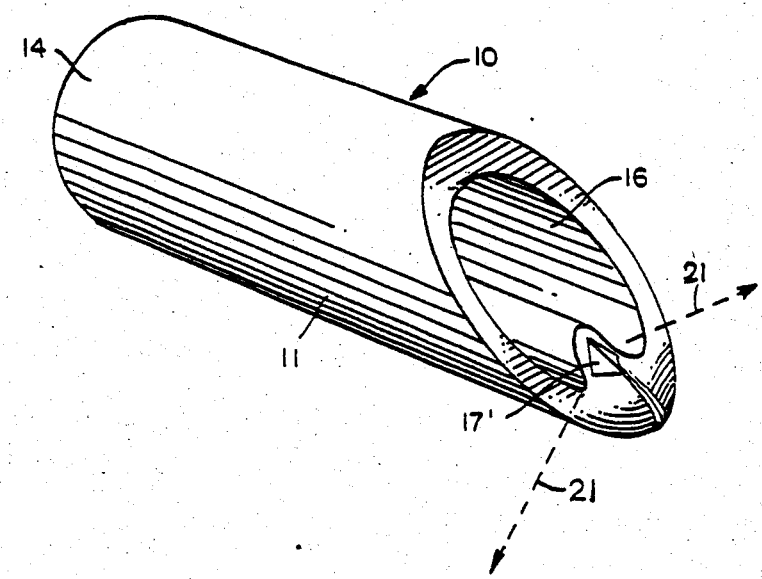
FIG. 5 is a perspective view of the tip portion of a second embodiment.

The embodiment of FIGS. 5 and 6 is identical to the one already disclosed except that emitter 17' takes the form of a prism capable of redirecting the light transmitted by the fiberoptic conductor in lateral directions as indicated by arrows 21. The limited number of planar faces of the prism (a prism having two such faces being illustrated) results in a greater concentration of light projected laterally from the emitter than is possible with a generally semi-spherical bead; hence, a laterally-directed beam from prism 17' passing at right angles through the patient's chest would be expected to be more easily seen than the more diffuse discharge of light from bead 17.

Figure 8:
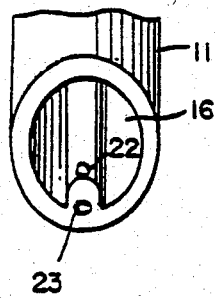
FIG. 8 is a top perspective view in reduced scale of the tip construction of FIG. 7.
Figure 7:
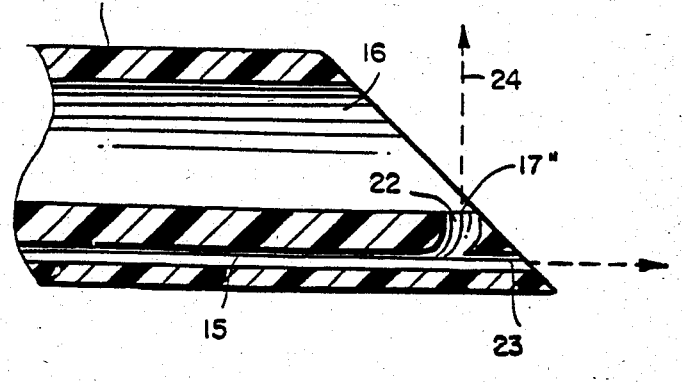
FIG. 7 is a longitudinal sectional view of the tip portion of a medical tube constituting a third embodiment of the invention.

The light emitter 17" of the embodiment illustrated in FIGS. 7 and 8 takes the form of a bifurcated end portion of fiberoptic light conductor 15. Two or more branches 22 and 23 are preferred, at least one of which projects light in a lateral direction as indicated by arrow 24.

FIGS. 9-12 depict a preferred embodiment of the invention in which endotracheal tube 110 has its wall 114 formed of a transparent, flexible, soft but tough plastic material which, in the absence of distorting forces, will assume, and will recover to, the curved configuration (known as a Magill curve) shown in FIG. 9. Polyvinyl chloride, or blends of polyvinyl chloride and polyvinyl acetate, have been found particularly effective but other clear plastic materials having similar properties may be used. The proximal end of the tube is joined to a connector 112 which in turn is adapted to be joined to a source 13 of an oxygen-air mixture.

The distal tip portion 111 of the tube is beveled, as described in connection with the previous embodiments, and, as shown most clearly in FIG. 10, the edges 111a of the wall 114 about the opening 116a for lumen 116 are rounded when viewed in longitudinal section so that there are no sharp edges engagable with the mouth and throat tissues of a patient. The angle of the bevel is shown to be approximately 45 degrees; however, that angle may be varied considerably.

The fiberoptic light conductor 115 extends longitudinally through the wall 114 of the tip portion 111 of the thermoplastic tube and continues in a proximal direction to an exit point 150 intermediate the tube's proximal and distal ends. Ideally, the portion 115a of the conductor disposed externally of tube 110 is sheathed in a protective thermoplastic tube 151 that may conveniently be formed of the same polymeric material as wall 114 of the main tube 110. The two tubes 110 and 151 may therefore be blended together by a suitable solvent cement, or by heat sealing, or by any other appropriate means, in exit zone 150.

As in previous embodiments, the proximal end of the light conductor couples to a suitable light source 18. Any suitable coupling means, such as plug-in connector 152, may be provided for detachably connecting the fiberoptic light conductor to source 18.

The fiberoptic light conductor 115 may be composed of a single fiber (as shown) or a bundle of such fibers, all as previously described. A single fiber of clear, light-transmitting plastic (e.g., polymethyl methacrylate) has been found particularly effective since no resolution or image-transmission is involved; however, other materials such as glass, or multiple fiber bundles, may also be used. Referring to FIGS. 10 and 12, it will be observed that the fiberoptic light conductor 115 has its distal end terminating in an end face 117 which serves as the emitter for directing light laterally from the tip portion of tube 110. The distal end of the conductor is totally embedded within the plastic wall 114 of the tube and, therefore, the smooth flexible plastic material protects a user against direct contact with the end of the fiberoptic light conductor. Since wall 114 is formed of transparent material, light emitted from end face 117 may pass outwardly from tip 111 notwithstanding the fact that the distal end portion of the conductor is completely embedded.

While a simplified form of emitter 117 is provided by the embodiment of FIGS. 9–12, it is to be understood that the prism 17' or bead 17 of previously-described embodiments may also be embedded within the transparent plastic material of wall 114 for the purpose of directing light laterally from the tip of the endotracheal tube. Regardless of the means used to direct light at the end of the fiberoptic conductor, direct contact between that conductor and the patient would be shielded by the transparent thermoplastic material of the tube 110 in which the distal end portion of the light conductor is embedded.

If desired, the tube 110 may also be provided with markings 153 at selected locations near the tip portion 111 to assist a user in the proper placement of the tube. Similar markings 154 accompanied by numerical indicia may be used to indicate the distance from the tip (usually in centimeters) so that a user may readily determine the extent of intubation.

The endotracheal tube of FIGS. 9–12 is used in the same manner described with respect to the other embodiments of this invention. High-intensity light in the visible spectrum is transmitted by the fiberoptic conductor to the tip portion of the tube where it is directed laterally with the result that point illumination occurs at the endotracheal tube's distal end. Some of the light projected laterally, including that light reflected by tissues surrounding the tip portion of the tube, passes through the body wall of the patient and may be externally observed by the naked eye, thereby permitting a qualified medical attendant to determine, and if necessary adjust, the anatomical position of the tip portion of the tube.

While in the foregoing, I have disclosed several embodiments of the invention in considerable detail for purposes of illustration, it will be understood by those skilled in the art that many of these details may be varied without departing from the spirit and scope of the invention.

I claim:

1. A method for locating the tip of an endotracheal tube inserted into a patient's trachea to provide an airway thereto, comprising the steps of introducing an endotracheal tube through a patient's mouth or nose, said tube having an air passage extending longitudinally therethrough to an opening at the distal tip thereof and also having means for emitting and laterally projecting a beam of high-intensity visible light from a point immediately adjacent said opening, advancing said tube so that the tip thereof enters the patient's trachea, and locating the position of the tip of said tube as it is advanced by externally and visually observing the light emitted from said tip and projected laterally through the body wall of said patient.

2. The method of claim 1 in which there is the further step of adjusting the position of said tube by shifting the same longitudinally while externally observing changes in the position of the point of light projected through said body wall of said patient.

3. The method of claim 1 which includes projecting said light from the distal end of said tube within the wavelength range of about 4000 to 7700 angstroms.

4. The method of claim 1 which includes projecting said light laterally from the tip of said tube through a transparent portion of the wall thereof.

5. The method of claim 1 which includes projecting said light laterally from only a single point immediately adjacent said opening of said tube.

* * * * *